(12) United States Patent
Leflaive et al.

(10) Patent No.: US 10,000,430 B2
(45) Date of Patent: Jun. 19, 2018

(54) PROCESS FOR SEPARATING PROPYLENE MIXED WITH PROPANE BY ADSORPTION IN A SIMULATED MOVING BED

(71) Applicant: IFP, Rueil Malmaison (FR)

(72) Inventors: Philibert Leflaive, Mions (FR); Luc Wolff, Chaponnay (FR); Damien Leinekugel Le Cocq, Lyons (FR); Nabil Lamia, Porto (PT); Alirio Rodrigues, Porto (PT); Carlos Grande, Porto (PT)

(73) Assignee: IFP ENERGIES NOUVELLES, Rueil Malmaison (FR)

( * ) Notice: Subject to any disclaimer, the term of this patent is extended or adjusted under 35 U.S.C. 154(b) by 0 days. days.

(21) Appl. No.: 14/722,715

(22) Filed: May 27, 2015

(65) Prior Publication Data

US 2015/0266797 A1 Sep. 24, 2015

Related U.S. Application Data

(63) Continuation of application No. 12/374,911, filed as application No. PCT/FR2007/001170 on Jul. 6, 2007.

(30) Foreign Application Priority Data

Jul. 24, 2006 (FR) ...................... 06 06827

(51) Int. Cl.
*C07C 7/13* (2006.01)
*B01D 53/04* (2006.01)

(52) U.S. Cl.
CPC ................ *C07C 7/13* (2013.01); *B01D 53/04* (2013.01); *B01D 2253/108* (2013.01); *B01D 2253/116* (2013.01); *B01D 2253/304* (2013.01); *B01D 2256/24* (2013.01); *B01D 2257/7022* (2013.01); *C10G 2400/20* (2013.01)

(58) Field of Classification Search
None
See application file for complete search history.

(56) References Cited

U.S. PATENT DOCUMENTS

| | | |
|---|---|---|
| 2,906,795 A | 9/1959 | Ballard et al. |
| 3,231,492 A | 1/1966 | Stine et al. |
| 5,744,687 A | 4/1998 | Ramachandran et al. |
| 6,293,999 B1 | 9/2001 | Cheng et al. |

FOREIGN PATENT DOCUMENTS

| | | |
|---|---|---|
| EP | 0 511 885 A1 | 11/1992 |
| FR | 2 704 158 A1 | 10/1994 |

OTHER PUBLICATIONS

Da Silva and Rodrigues, Adsorption Equilibria and Kinetics for Propylene and Propane over 13X and 4A Zeolite Pellets, Ind. Eng. Chem. Res., vol. 38, p. 2051-2057, 1999.

D.L. Peterson et al., "Separation of Propylene and Propane on Molecular Sieves by Vicinal Exchange Sorption", Molecular Sieves Proceedings, XP001536328 (1967, 1968) pp. 217-230.

*Primary Examiner* — Tam M Nguyen
(74) *Attorney, Agent, or Firm* — Millen, White, Zelano, Branigan, P.C.

(57) ABSTRACT

A process for separating propylene mixed with propane by adsorption in a simulated moving bed is described. The process operates in the gaseous phase or in the liquid phase, and it uses a 13X faujasite-type zeolite as adsorbent solid and butene-1 or isobutane or any mixture of these 2 components as desorbent.

7 Claims, 4 Drawing Sheets

Figure 1:
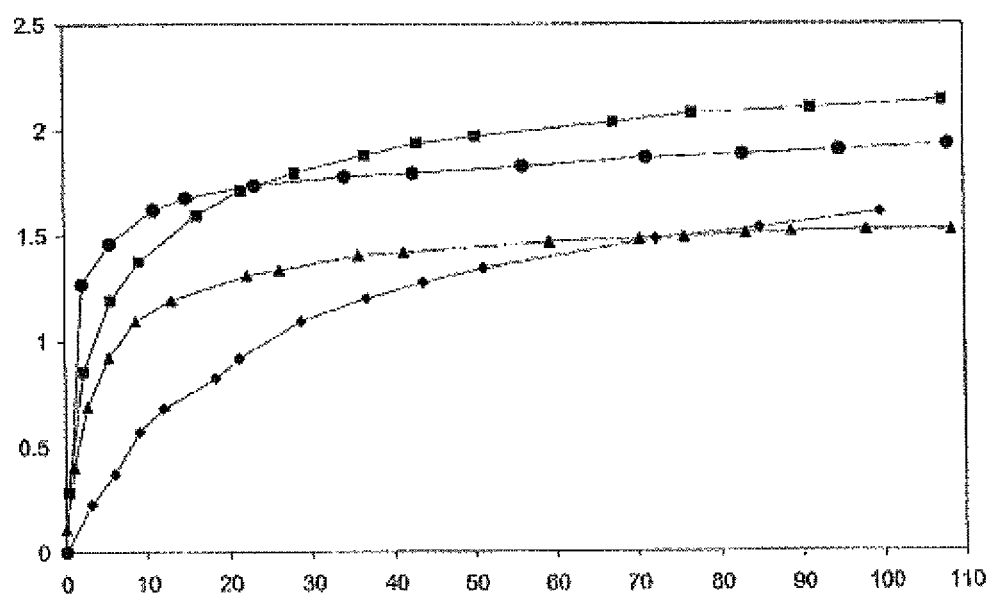

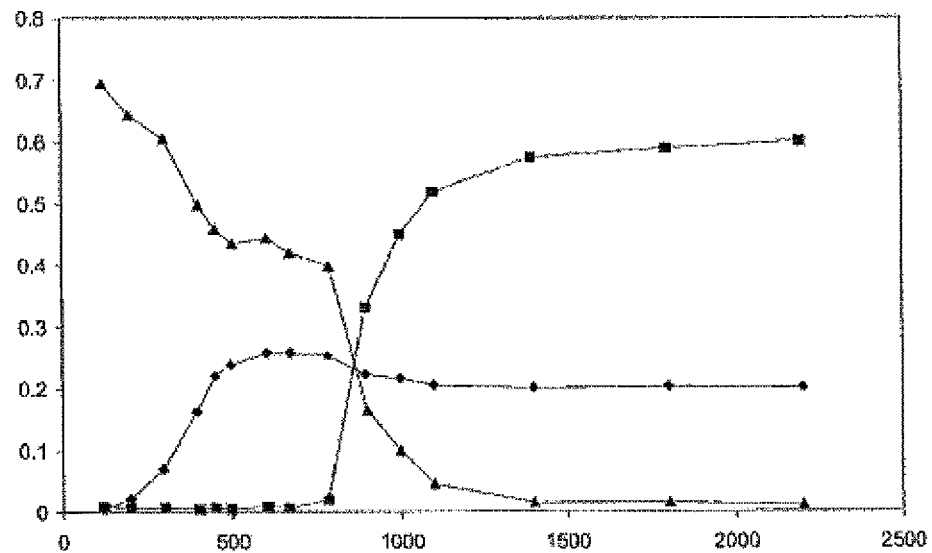
Figure 2
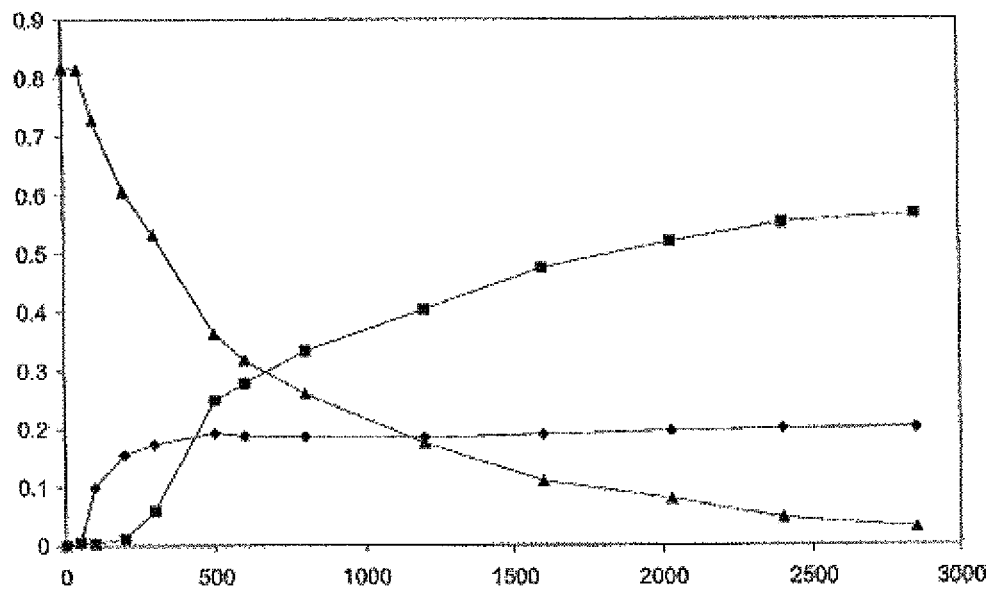
[Figure 2a]

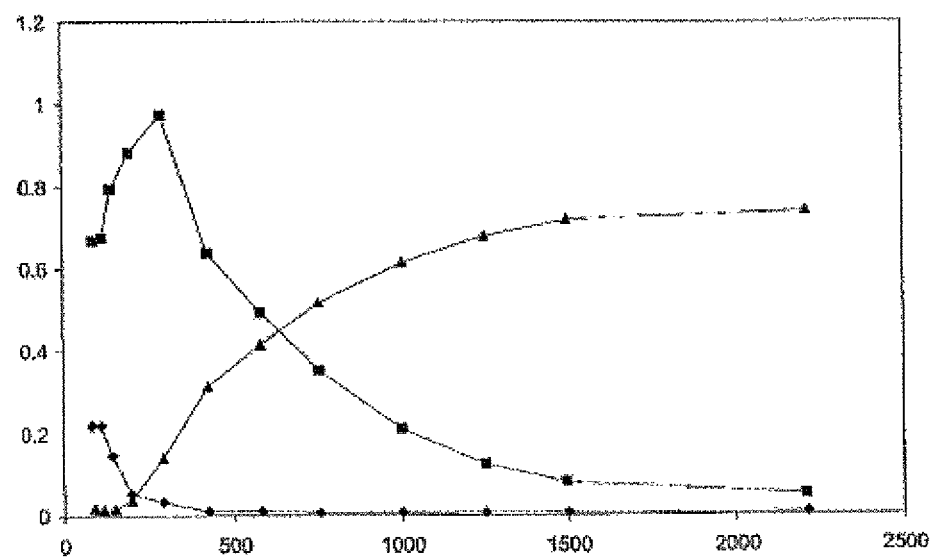
Figure 3
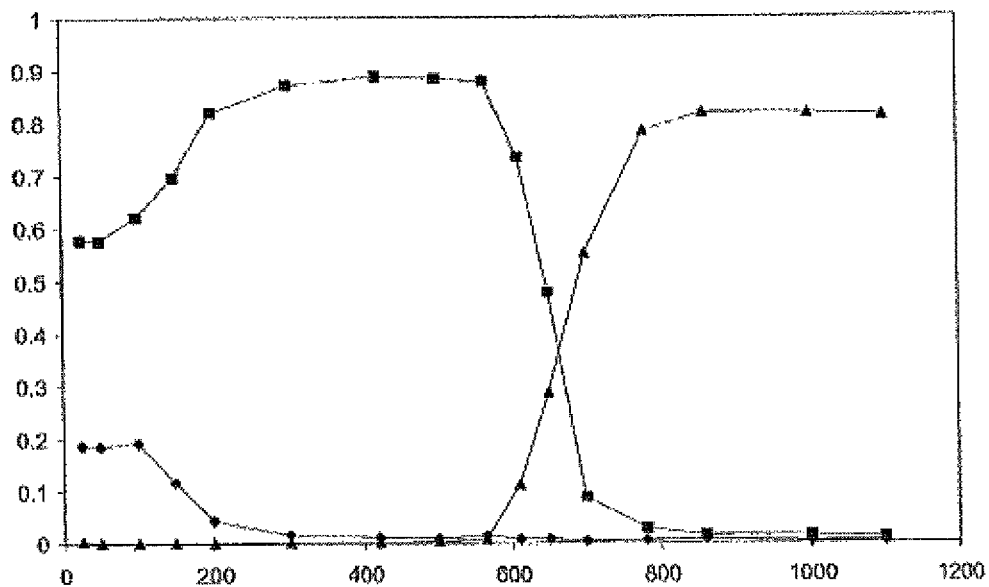
[Figure 3a]

PROCESS FOR SEPARATING PROPYLENE MIXED WITH PROPANE BY ADSORPTION IN A SIMULATED MOVING BED

FIELD OF THE INVENTION

The invention relates to a process for the production of propylene from a feedstock that contains essentially propane and propylene. This feedstock can also contain, in a minority portion, other hydrocarbons that are heavier or lighter than the C3 hydrocarbons. These hydrocarbons other than C3 can represent up to 10% by weight of the feedstock to be treated, and preferably represent less than 5% by weight of the feedstock that is to be treated.

This invention applies in particular to the production of propylene with a high level of purity and with a high yield. Propylene with a high level of purity is defined as a purity level that is greater than 95.0% by weight, and preferably greater then 97% by weight.

EXAMINATION OF THE PRIOR ART

Propylene is an important intermediate compound in the field of petrochemistry, and it intervenes in particular in the production of polypropylene, acrylonitrile, isopropanol, cumene and oxo alcohols.

Propylene is primarily produced by steam-cracking or by catalytic cracking of heavy fractions, and it is generally obtained mixed with propane. Heavy fraction is defined as a hydrocarbon fraction that typically has a distillation interval of between 200° C. and 450° C., such as, for example, a vacuum distillate or an atmospheric residue. In a general way, any petroleum fraction regardless of its origin, containing for the most part propane and other C3 hydrocarbons, is able to constitute a feedstock for the process according to the invention.

So as to upgrade the propylene, it is necessary to eliminate the propane. Currently, this separation stage or super-fractionating stage is ensured on the industrial scale by distillation. The boiling points of propane and propylene being very close, this stage of super-fractionation by distillation requires a very large number of theoretical stages, which brings about very high energy consumption.

The production of propylene by selective adsorption was the object of numerous studies. We cite, for example, that of Da Silva and Rodrigues (1999, Ind. Eng. Chem. Res., Vol. 38, p. 2051) who compare the adsorption of propane and propylene on 13X- and 4A-type zeolites and that of Grande and Rodrigues (2001, Ind. Eng. Chem. Res., Vol. 40, p. 1686) who study the adsorption on silica gel, or else Grande, Gigola and Rodrigues (2002, Ind. Eng. Chem. Res., Vol. 41, p. 85) who studied the adsorption on the 5A zeolite.

The processes for separation by adsorption that use methods for desorbing propylene by action on the temperature and pressure parameters are well known from the prior art. By way of example, we cite the patent U.S. Pat. No. 2,642,153 based on a high-temperature desorption, and the patent U.S. Pat. No. 6,296,688 based on a low-pressure regeneration.

The TSA processes (abbreviation of "Temperature Swing Adsorption" that can be translated by "adsorption process by temperature variation") use a high-temperature regeneration of the adsorbent solid and generally have low productivities and yields.

In addition, the high temperature conditions, generally beyond 200° C., are able to accelerate the degradation of the performance levels of the molecular sieve. The patent U.S. Pat. No. 6,293,999 and the study by Rao et al. (2005, J. Chromato A, Vol. 1069, p. 141) have in common to propose processes based on the implementation in a simulated moving bed in the gaseous phase in which the regeneration of the adsorbent by a desorbent is replaced by a regeneration by pressure modulation, i.e., performed under vacuum.

This type of vacuum regeneration brings about a high power consumption.

In addition, the propylene is obtained at low pressure.

The prior art notes only a single study that aims at using a desorbent to desorb propylene during a separation of propane/propylene on the adsorbent solid. Peterson, Helfferich and Griep (Molecular Sieves Proc. 1$^{st}$ Int. Zeolite Conf. London 1967, published by Soc. Chem. Ind., London 1968, First International Conference on Molecular Sieves and Zeolites in 1967 in London) proposed an isothermal and isobaric process for adsorption in the gaseous phase, with concentration modulation, which is based on alternating adsorption stages and desorption stages using desorbent. The adsorbent that is selected for this study is a 5A zeolite. The n-butane and the n-pentane have been tested as desorbent. The use of a 5A zeolite poses aging problems due to the formation of coke that is deposited inside the pores of the 5A zeolite. To limit this phenomenon, an addition of ammonia is necessary. This therefore introduces an additional radical that has to be eliminated from the propylene that is produced.

As adsorbent, this invention also comprises a 13X zeolite, less active than the 5A zeolite that does not exhibit deactivation problems and therefore does not require an addition of ammonia.

It is well known that the 5A zeolite contains acid sites that are responsible for the formation of coke when it is sought to adsorb olefins. It is possible to consult, for example, Misk, Joly, Magnoux et al. (2000, Microporous and Mesoporous Materials, Vol. 40, p. 197, a journal whose French title is "Materiau micro et mesoporeux)," Magnoux, Misk, Joly, et al. (1996, Zeolites, Vol. 16, p. 265).

The fact that the 13X zeolite does not exhibit aging constitutes a surprising effect, given that Martra, Coluccia, Davit et al. (1999, Research on Chemical Intermediates, Vol. 25, p. 77, whose French title is "Recherche sur les intermediaires chimiques") demonstrate by spectroscopy the existence of the Bronsted acid hydroxyl groups that are well known to one skilled in the art for generally facilitating the formation of coke.

The patent FR 2,704,158 describes a process for fractionating a mixture in a gaseous-phase simulated moving bed. In a general manner, this patent describes a category of processes for separation by adsorption, without any specific teaching on the separation of a propane/propylene mixture.

In a process for adsorption with regeneration of the adsorbent solid, the selection of the desorbent is generally done according to three criteria:

On the one hand, the desorbent is to have a boiling point that is far from the products to be separated, so as to be able to recover the desorbent by distillation;

On the other hand, the desorbent is preferably to exhibit an isotherm that is close to that of product (A) that has the most affinity with the adsorbent so as to limit the quantity of desorbent necessary to desorb this product (A);

Finally, the desorbent is preferably to be a little less adsorbed than the product (A) so that at the feedstock injection, the product (A) displaces the desorbent and thus can be adsorbed.

The object of this invention is to present a process for separating propylene mixed with propane, implemented in a simulated moving bed in the gaseous phase or in the liquid phase, using a 13X faujasite-type zeolite as an adsorbent and a hydrocarbon that comprises 4 or 5 carbon atoms (C4 or C5 hydrocarbons) as desorbent. This process does not exhibit aging of the adsorbent and makes it possible to reach a high yield and a high productivity of propylene with low energy consumption.

The document U.S. Pat. No. 3,231,492 describes a process for separating the propylene that is contained in a propane-propylene mixture that is implemented in a simulated moving bed, whereby the adsorbent solid is a 5A zeolite, and the desorbent that is used is n-butane. This process is a process in liquid phase only, contrary to the process according to this invention that can operate in the gaseous phase.

SUMMARY DESCRIPTION OF THE FIGURES

FIG. 1 has adsorption isotherms of propylene, propane, isobutane and butene-1 at 373K on a 13X zeolite. The adsorbed quantity (on the ordinate) is expressed in millimols per gram of adsorbent solid, and the pressure (on the abscissa) is expressed in kilopascal (1 kilopascal=$10^3$ Pascal).

The curve with squares corresponds to propylene, the one with triangles corresponds to isobutane, the one with diamonds corresponds to propane, and the one with dots corresponds to butene-1.

FIG. 2 provides a view of the piercing curve on an isobutane-saturated bed of a propylene/propane mixture (75 mol %/25 mol %) at 373K and 1.5 bar (1 bar=$10^5$ Pascal), on a 13X sieve. The partial molar flow rate (on the ordinate) is expressed in millimols per second, and the time (on the abscissa) is expressed in seconds.

The curve with squares corresponds to propylene, the one with triangles corresponds to isobutane, and the one with diamonds corresponds to propane.

FIG. 2a provides a view of the piercing curve on a butene-1-saturated bed of a propylene/propane mixture (75 mol %/25 mol %) at 373K and 1.5 bars (1 bar=$10^5$ Pascal), on a 13X sieve. The partial molar flow rate (on the ordinate) is expressed in millimols per second and the time (on the abscissa) is expressed in seconds.

The curve with squares corresponds to propylene, the one with triangles corresponds to isobutane, and the one with diamonds corresponds to butene-1.

FIG. 3 provides a view of the punch-through curve on a bed that is saturated with a propylene/propane mixture (75 mol %/25 mol %) at 373K and 0.15 MPA on a 13X faujasite-type zeolite with isobutane as a desorbent.

The partial molar flow rate (on the ordinate) is expressed in millimols per second, and the time (on the abscissa) is expressed in seconds.

The curve with squares corresponds to propylene, the one with triangles corresponds to isobutane, and the one with diamonds corresponds to propane.

FIG. 3a provides a view of the punch-through curve on a bed that is saturated with a propylene/propane mixture (75 mol %/25 mol %) at 373K and 0.15 MPa on a 13X faujasite-type zeolite with the butene-1 as desorbent.

The molar partial flow rate (on the ordinate) is expressed in millimols per second, and the time (on the abscissa) is expressed in seconds.

The curve with squares corresponds to polypropylene, the one with triangles corresponds to butene-1, and the one with diamonds corresponds to propane.

Figure 4:
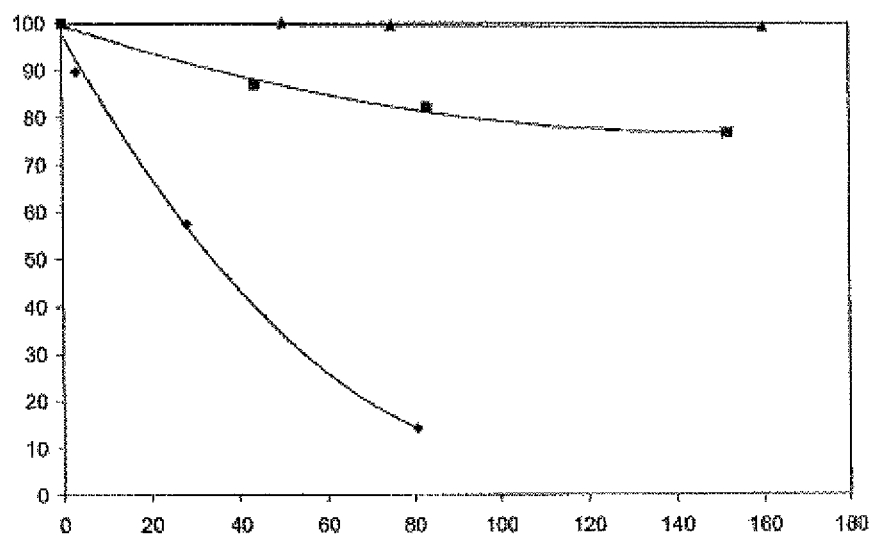

FIG. 4 provides a view with a loss of capacity over time of a 5A zeolite and a 13X zeolite, at 458K and 1.83 MPa over a propylene feedstock.

The ratio between the capacity of the sieve at a given moment and the initial capacity of the sieve (on the ordinate) is expressed in percentages, and the time (on the abscissa) is expressed in hours.

The curve with diamonds corresponds to the 5A zeolite without ammonia, the one with squares corresponds to the 5A zeolite with 0.25% by weight of ammonia, and the one with triangles corresponds to the 13X zeolite.

DESCRIPTION OF THE INVENTION

The invention relates to a process for the production of high-purity propylene by adsorption from a feedstock that contains mostly a mixture of propane and propylene, whereby this feedstock is typically obtained by steam-cracking or fluidized bed catalytic cracking (denoted FCC in abbreviated form), optionally after selective hydrogenation that makes it possible to reduce its diolefin content.

A typical example of feedstock that can be used in this separation process is a C3 fraction that is obtained from fractionation of an FCC unit.

The process according to the invention makes use of the technique of the simulated moving bed that is well described in particular in the patent FR 2 704 158.

The simulated moving bed unit according to the invention will comprise between 4 and 24 beds and preferably between 6 and 20 beds of adsorbent solid. Of course, one industrial unit can comprise several units or columns that operate in series and/or in parallel.

The process according to the invention can operate in the gaseous phase or in the liquid phase and comprises the following stages:
 a) A stage for bringing the feedstock into contact with an adsorbent bed that contains 13X zeolite so as to preferably adsorb the propylene;
 b) A stage for bringing the adsorbent bed into contact with a desorbent, whereby said desorbent is either butene-1 or isobutane,
 c) A stage for drawing off from the adsorbent bed a flow that contains the desorbent and the least selectively adsorbed products of the feedstock,
 d) A stage for drawing off from the adsorbent bed a flow that contains the desorbent and the propylene.

The process can optionally include one of the two following stages or the following two stages:
 e) A stage for separating the flow from stage c) into a first flow that contains the desorbent and a second flow that contains the products of the feedstock that are the least selectively adsorbed,
 f) A stage for separating the flow from stage d) into a first flow that contains the desorbent and a second flow that contains the high-purity propylene.

High-purity propylene is defined as a propylene content in the effluent of this separation process that is greater than or equal to 90% by weight, and preferably greater than 95% by weight.

This invention is based on the selection of an adsorbent/desorbent pair that has proven particularly high-performing both in yield and in service life relative to the pairs already disclosed.

The selected adsorbent is a 13X faujasite zeolite that has a good propane/propylene selectivity and does not have an aging problem.

The selected desorbent is either butene-1, or isobutane, or a mixture in any proportion of these two components.

The process according to this invention can operate both in the gaseous phase as well as in the liquid phase with a suitable selection of operating conditions and the shaping of the adsorbent solid.

During the operation of the process according to the invention in the gaseous phase, the adsorbent is preferably in the form of extrudates with a diameter of between 1 mm and 2 mm, and with a length of between 2 mm and 16 mm. The pressure is between 0.1 MPa and 1 MPa, and the temperature is between 20° C. and 150° C.

During the operation of the process according to the invention in the liquid phase, the adsorbent is preferably in the form of balls, with a diameter of between 0.6 mm and 2 mm. The pressure is between 0.8 MPa and 2 MPa, and the temperature is between 0° C. and 60° C.

EXAMPLES

The invention will be better understood from reading the following examples that illustrate the invention without, however, limiting the scope thereof.

The examples present the results of measurements of adsorption isotherms and of piercing/punch-through tests of a propane/propylene mixture with the isobutane as desorbent.

Example 1

In this example, the adsorption isotherms of propylene, propane and isobutane on a 13X faujasite-type zeolite are measured gravimetrically at 373K.

The measured isotherms are provided in FIG. 1.

FIG. 1 shows the adsorption isotherms of propylene, propane, isobutane and butene-1 at 373K on a 13X zeolite.

The adsorbed quantity (on the ordinate) is expressed in millimols per gram of adsorbent solid, and the pressure (on the abscissa) is expressed in kilopascal (1 kilopascal=$10^3$ Pascal).

The curve with squares corresponds to propylene, the one with triangles corresponds to isobutane, the one with diamonds corresponds to propane, and the one with dots corresponds to butene-1.

The results that are obtained at 373K show that isobutane and butene-1 are slightly less adsorbed than propylene and more adsorbed than propane.

These results indicate that isobutane and butene-1 have suitable adsorption isotherms to be used as desorbent in a simulated moving bed process for separating the propylene from propane. Actually, the fact that isobutane and propylene have an isotherm that is close to the one of propylene ensures that the quantity of desorbent that is necessary to desorb the propylene is not too high.

In addition, the fact that isobutane and butene-1 are slightly less adsorbed than the propylene ensures that the propylene that is injected at the feedstock displaces the isobutane or the butene-1, and therefore that the propylene is properly adsorbed.

Example 2

In this example, the separation of the propylene (piercing and punch-through curve) from a propylene/propane mixture is evaluated at 373K, on a 13X faujasite-type zeolite. The adsorbent bed has a length of 0.84 m, with an inside diameter of 2.15 cm. The void fraction of the bed or interstitial porosity is 0.395.

The activation of the adsorbent is carried out in-situ by injecting a flow of nitrogen of 60 liters/hour in standard conditions (273K and 0.1 MPa). The temperature is then increased linearly along a slope of 1K/minute until reaching 593K.

The temperature is then kept at 593K for 12 hours.

The operating mode for obtaining the piercing and punch-through curves is as follows:

Injection of solvent under target conditions of temperature and pressure (373K and 0.15 MPa), at 1 liter/minute under standard conditions.

Solvent/feedstock switching to inject the feedstock (1 liter/minute under standard conditions).

The injection of the feedstock is then maintained for an adequate period of time to reach the thermodynamic equilibrium.

Collection and analysis of the piercing effluent.

Then for the punch-through:

Feedstock/solvent switching for injecting the solvent (1 liter/minute under standard conditions).

The injection of solvent is maintained for an adequate time to desorb all of the compounds of the feedstock.

Collection and analysis of the punch-through effluent.

During the test, the temperature of the column is maintained at 373K and the pressure at 0.15 MPa.

During the piercing and punch-through, the effluent from the column is sampled (15 samples during the piercing and 12 samples during the punch-through), then analyzed by gas chromatography so as to determine its composition at different time intervals.

The composition of the feedstock is:
Propylene: 75 mol %
Propane: 25 mol %

The piercing and punch-through curves are provided by FIGS. 2 and 3. The curve with squares corresponds to propylene, the one with triangles corresponds to isobutane, and the one with diamonds corresponds to propane.

The results that are obtained show that the propylene/isobutane selectivity is particularly good for an optimized operation of a process for separating propylene by adsorption. Actually, propylene easily displaces isobutane, and isobutane makes possible a good desorption of propylene. In addition, it is noted that the fronts are not very dispersed and that the tracks are weak, which facilitates separation.

Example 2a

This example is similar in all respects to Example 2, except that isobutane is replaced by butene-1.

The piercing and punch-through curves are provided by FIGS. 2a and 3a. The curve with squares corresponds to propylene, the one with triangles corresponds to butene-1, and the one with diamonds corresponds to propane.

FIG. 2a provides a view of the piercing curve on a bed that is saturated with butene-1 of a propylene/propane mixture (75 mol %/25 mol %) at 373K and 1.5 bar (1 bar=$10^5$ Pascal), on a 13X sieve. The partial molar flow rate (on the ordinate) is expressed in millimols per second, and the time (on the abscissa) is expressed in seconds.

The results that are obtained show that the propylene/butene-1 selectivity is particularly good for an optimized operation of a process for separating propylene by adsorption. Actually, the propylene easily displaces butene-1, and butene-1 allows a good desorption of propylene. In addition, it is noted that the fronts are not very dispersed, and the tracks are weak, which facilitates separation.

FIG. 3a provides a view of the punch-through curve on a bed that is saturated with a propylene/propane mixture (75 mol %/25 mol %) at 373K and 0.15 MPa, on a 13X faujasite-type zeolite with butene-1 as desorbent.

The partial molar flow rate (on the ordinate) is expressed in millimols per second, and the time (on the abscissa) is expressed in seconds.

The curve with squares corresponds to propylene, the one with triangles corresponds to butene-1, and the one with diamonds corresponds to propane.

Example 3

In this example, the aging of the 13X faujasite zeolite is studied and compared to that of the 5A zeolite. For this purpose, the bed is kept at 458K and 1.83 MPa. A propylene flow rate of 0.5 liter/minute is imposed under standard conditions, and the evolution of the adsorption capacity of the sieve is gravimetrically measured regularly.

The results that are obtained are provided in FIG. 4.

FIG. 4 provides a view of the loss in capacity over time of a 5A zeolite and a 13X zeolite, at 458K and L83 MPa on a propylene feedstock.

The ratio between the capacity of the sieve at a given moment and the initial capacity of the sieve (on the ordinate) is expressed by percentages, and the time (on the abscissa) is expressed in hours.

The results that are obtained show that the 5A zeolite has an aging problem, even in the presence of ammonia, while the 13X zeolite, used without the addition of ammonia, does not have a significant capacity loss over the duration of the test.

The invention claimed is:

1. A process for separating propylene by adsorption from a hydrocarbon mixture that contains at least 90% by weight of propylene and propane, wherein said hydrocarbon mixture optionally additionally comprises other hydrocarbons, wherein said process is implemented in a simulated moving bed in the gaseous phase and implements a 13X faujasite-type zeolite as an adsorbent solid and implements butene-1, isobutene, or a mixture of butene-1 and isobutene as desorbent, said process comprises:
   a) a stage wherein the hydrocarbon mixture is brought into contact with an adsorbent bed that contains 13X zeolite to adsorb the propylene;
   b) a stage wherein the adsorbent bed is brought into contact with the desorbent,
   c) a stage wherein a flow that contains desorbent and the least selectively adsorbed products of the hydrocarbon mixture are drawn off from the adsorbent bed,
   d) a stage wherein a flow that contains desorbent and propylene are drawn off from the adsorbent bed,
   e) a stage wherein the flow from stage c) is separated into a first flow that contains the desorbent and a second flow that contains the least selectively adsorbed feedstock products, wherein the desorbent is recycled at the inlet of the simulated moving bed unit, and
   f) a stage wherein the flow from stage d) is separated into a first flow that contains the desorbent and a second flow that contains high-purity propylene, wherein the desorbent is recycled at the inlet of the simulated moving bed unit,
   wherein the bed is kept at about 458K and about 1.83 MPa, and a propylene flow rate of 0.5 liter/minute is imposed under standard conditions.

2. The process for separating propylene according to claim 1, in which the desorbent is isobutane.

3. The process for separating propylene according to claim 1, in which the adsorbent solid is in the form of extrudates with a diameter of between 1.0 and 2.0 mm, and with a length of between 2.0 and 16.0 mm.

4. The process for separating propylene according to claim 1, in which the adsorbent solid is shaped like balls with a diameter of between 0.6 and 2.0 mm.

5. The process for separating propylene according to claim 1, wherein the hydrocarbon mixture consists essentially of propylene and propane.

6. A method for separating propylene by adsorption from a hydrocarbon mixture comprising:
   a) contacting a hydrocarbon mixture with an adsorbent bed kept at 458K and 1.83 MPa that contains 13X faujasite-type zeolite to adsorb a propylene wherein said hydrocarbon mixture contains at least 90% by weight of propylene and propane, and a propylene flow rate of 0.5 liter/minute is imposed under standard conditions;
   b) contacting the adsorbent bed with a desorbent wherein said desorbent is butene-1 or isobutene or a mixture of butene-1 or isobutene,
   c) drawing off a flow that contains desorbent and the least selectively adsorbed products of the hydrocarbon mixture from the adsorbent bed,
   d) drawing off a flow that contains desorbent and propylene from the adsorbent bed,
   e) separating the flow that contains desorbent and the least selectively adsorbed products of the hydrocarbon mixture into a first flow that contains the desorbent and a second flow that contains the least selectively adsorbed feedstock products, wherein the desorbent is recycled at the inlet of the simulated moving bed unit, and
   f) separating the flow that contains desorbent and propylene into a first flow that contains the desorbent and a second flow that contains high-purity propylene, wherein the desorbent is recycled at the inlet of the simulated moving bed unit,
   wherein the process is implemented in a simulated moving bed in the gaseous phase at a temperature of between 20° C. and 150° C., and a pressure of between 0.1 and 1 MPa.

7. The method for separating propylene according to claim 6, in which the adsorbent solid is in the form of extrudates with a diameter of between 1.0 and 2.0 mm, and with a length of between 2.0 and 16.0 mm.

* * * * *